United States Patent [19]
Kingsley et al.

[11] Patent Number: 6,084,125
[45] Date of Patent: Jul. 4, 2000

[54] PROCESS FOR PRODUCING ALIPHATIC ACIDS USING A REACTOR SYSTEM HAVING A SHELL AND A TUBE REACTOR CONFIGURATION TO FORCE CIRCULATION OF REACTION LIQUID

[75] Inventors: Jeffrey Paul Kingsley, East Amherst; Mitchell Adis, North White Plains; Friedrich E. Purkert, Carmel, all of N.Y.

[73] Assignee: Praxair Technology, Inc., Danbury, Conn.

[21] Appl. No.: 09/120,728

[22] Filed: Jul. 23, 1998

Related U.S. Application Data

[63] Continuation-in-part of application No. 08/607,729, Feb. 27, 1996, Pat. No. 5,846,498.

[51] Int. Cl.[7] .................................................. C07C 51/16
[52] U.S. Cl. ...................... 562/531; 562/536; 562/498; 562/503; 562/505; 562/506; 562/509
[58] Field of Search .................... 562/531, 536, 562/498, 503, 505, 506, 509

[56] References Cited

U.S. PATENT DOCUMENTS

| | | | |
|---|---|---|---|
| 2,134,571 | 10/1938 | Morlock | 422/227 |
| 2,194,666 | 3/1940 | Meissner | 422/227 |
| 3,028,227 | 4/1962 | Ballestra | 422/227 |
| 4,449,828 | 5/1984 | Mansour | 366/147 |
| 4,676,953 | 6/1987 | Jeromin et al. | 422/106 |
| 4,798,131 | 1/1989 | Ohta et al. | 99/277.2 |
| 4,900,480 | 2/1990 | Litz et al. | 261/36.1 |
| 4,919,849 | 4/1990 | Litz et al. | 261/36.1 |
| 5,248,613 | 9/1993 | Roubicek | 435/315 |
| 5,395,593 | 3/1995 | Martin | 422/128 |
| 5,451,349 | 9/1995 | Kingsley | 261/91 |
| 5,503,220 | 4/1996 | Wood et al. | 165/108 |

Primary Examiner—Gary Geist
Assistant Examiner—Robert W. Deemie
Attorney, Agent, or Firm—Bernard Lau

[57] ABSTRACT

A shell and tube heat exchanger reactor with forced circulation is used to improve heat and mass transfer for exothermic liquid—liquid, gas-liquid and gas-liquid-solid reactions. Enhanced productivity and selectivity are obtained.

16 Claims, 8 Drawing Sheets

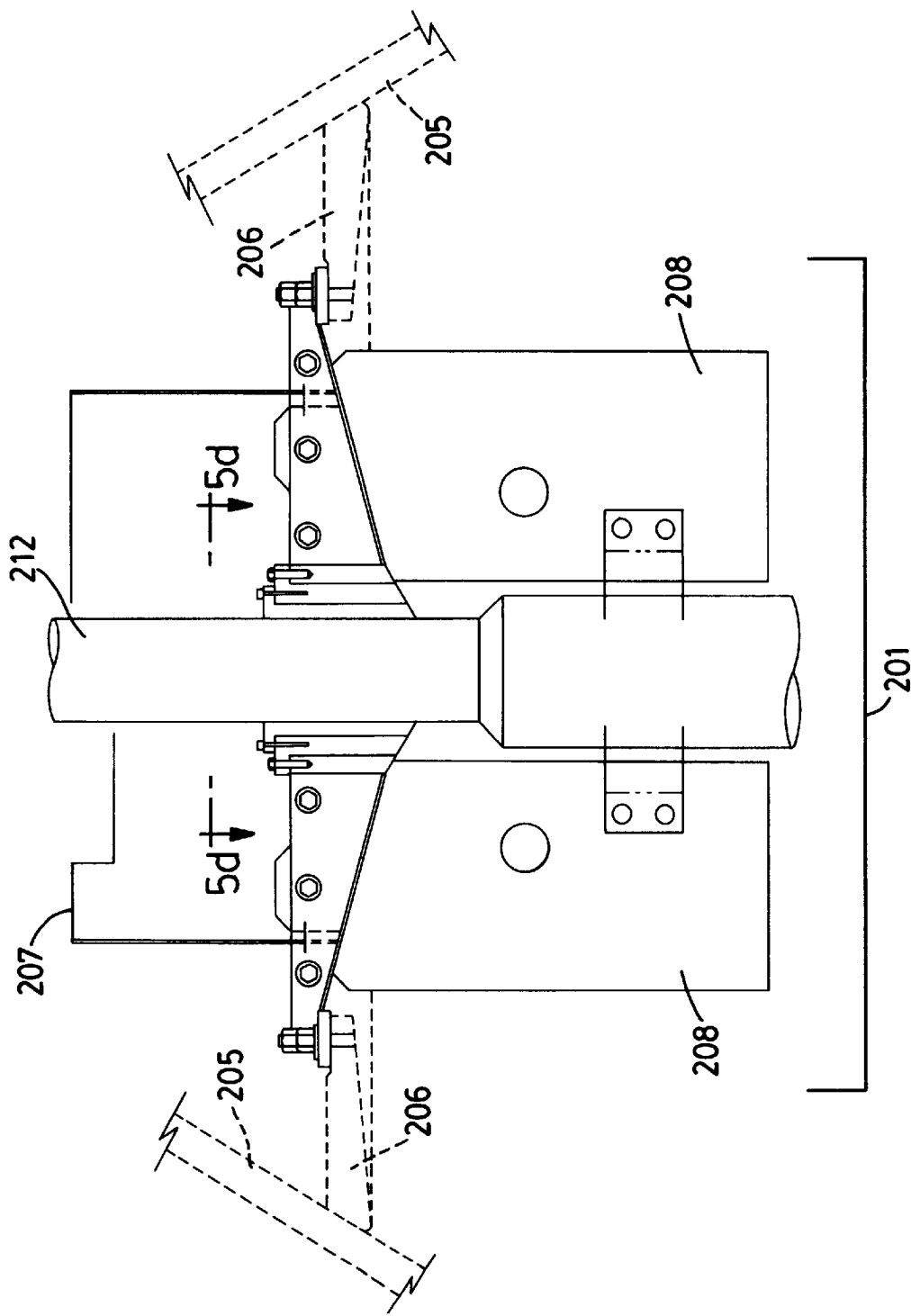

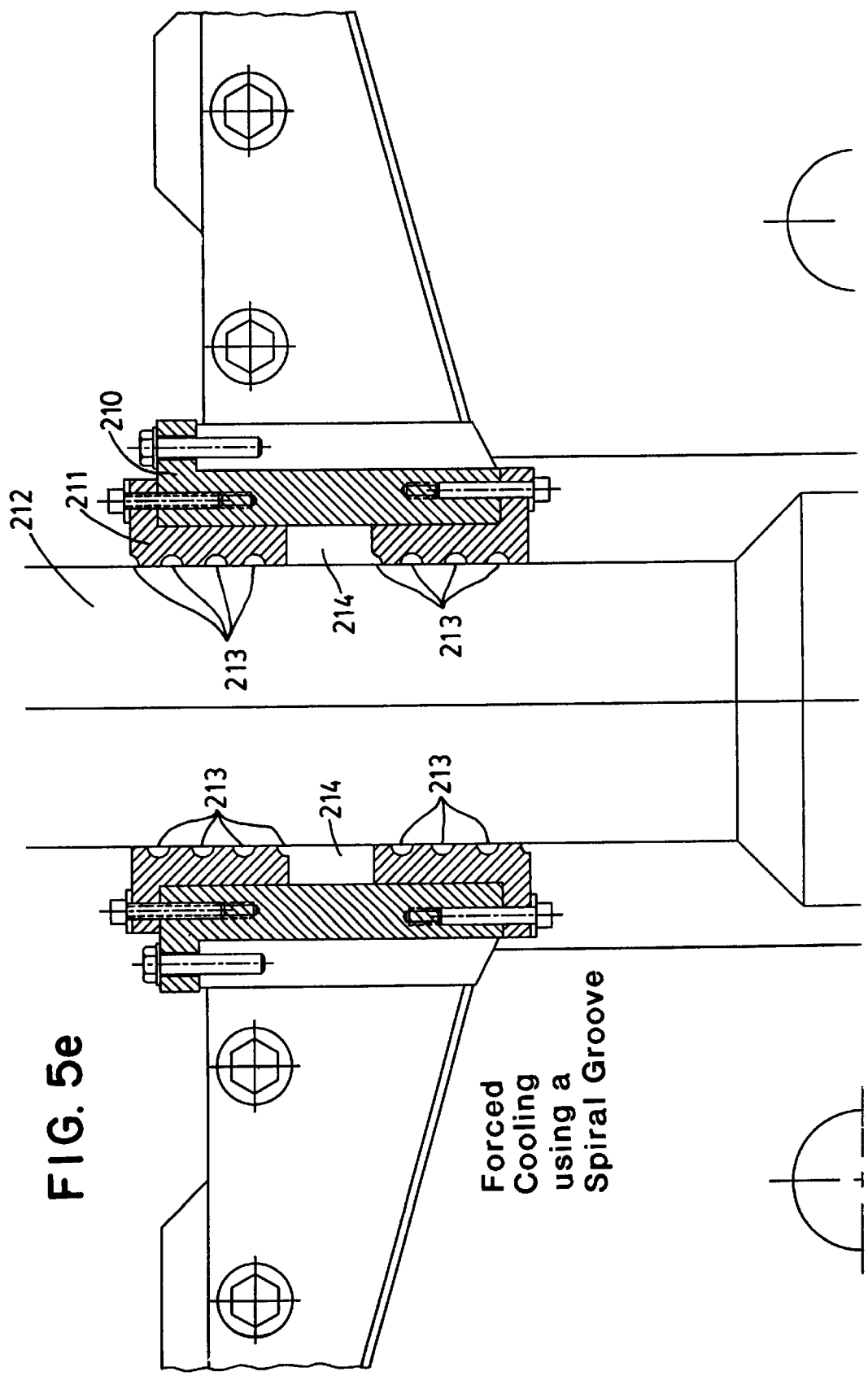

PROCESS FOR PRODUCING ALIPHATIC ACIDS USING A REACTOR SYSTEM HAVING A SHELL AND A TUBE REACTOR CONFIGURATION TO FORCE CIRCULATION OF REACTION LIQUID

This Appln is a CIP of application Ser. No. 08/607,729 filed Feb. 27, 1996 now U.S. Pat. No. 5,846,498.

BACKGROUND OF THE INVENTION

Description of the Prior Art

Many liquid phase oxidation and hydrogenation reactions carried out in commercial operations are highly exothermic in nature. In such operations, the ability to remove the heat of reaction very often limits the production rate obtainable for a given reactor volume. Exothermic reaction with heat removal is typically accomplished in a stirred tank reactor with a cooling jacket, a stirred tank reactor with internal cooling coils, a stirred tank reactor with an external sidestream cooling system, or a bubble column reactor with heat transfer tubes. In all cases, the heat of reaction is transferred from hot reaction liquid through a solid surface into a cooler fluid such as cooling water, a refrigerant, or to evaporate water to make steam.

Heat transfer in all of these systems is described by the following equations $$Q = rH_r V \quad (1);$$

$$Q = UA\Delta T \quad (2);$$

and hence:

$$rH_r = (A/V)U\Delta T \quad (3);$$

where Q is the total heat load, r is the volumetric reaction rate, $H_r$ is the heat of reaction, V is the reactor volume, U is the overall heat transfer coefficient, A is the heat transfer surface area and $\Delta T$ is the temperature difference between the reactor liquid and the heat transfer fluid. The left side of equation 3 is the volumetric heat of reaction or heat generation of the reactor, while the right side is the volumetric heat transfer capacity.

Equation 3 shows that heat generation increases with reaction rate and that, for steady state operation, the heat transfer capacity of the system must be increased when the reaction rate is increased. The equation also shows that heat transfer capacity is maximized when (1) the ratio of heat transfer area to reactor volume is maximized, (2) when the overall heat transfer coefficient U is maximized, and (3) when the temperature driving force $\Delta T$ is maximized.

The area to volume ratio A/V is fixed by the geometry of the reactor and heat exchange system.

The heat transfer coefficient U is a function of fluid properties, and to a lesser extent the materials of construction of the heat exchanger. U can be increased or decreased by increasing or decreasing the flow rates of the reaction fluid and/or the heat transfer fluid. Cooling fluid flows are usually limited by pressure drop and in some cases by temperature considerations. Depending on the heat transfer system, the reaction liquid flow rate is limited by power input to the agitator or by pressure drop considerations.

The temperature difference $\Delta T$ can be increased by increasing the reaction temperature and/or by decreasing the cooling fluid temperature. The reaction temperature is usually fixed so as to provide a given reaction rate and/or to minimize by-product formation. Thus, it is not usually desirable to raise the reaction temperature. The temperature of the cooling fluid is usually limited by the temperature of available cooling water, the cost of refrigeration or steam quality in evaporation systems.

In conventional reactor systems for exothermic reactions, a fundamental characteristic of jacketed reactor vessels is that they have a small A/V ratio. Since A increases as D, where D is the reactor diameter, and V increases as $D^2$, A/V decreases as the size of the reactor is increased. Thus, jacketed reactors are typically used in small volume applications up to 100 gallons.

Stirred tank reactors with internal cooling coils typically have a higher ratio of A/V than jacketed vessels, particularly as the vessel sizes get larger. However, coils have several limitations. Heat transfer area is maximized by minimizing coil diameter, but pressure drop in the coil gives a lower limit for the coil diameter. It is possible to increase A/V by packing the reactor with coils. However, this tends to cause uneven flow distribution in the reactor which can lead to poor reactant mixing and undesirable by-product formation. It is also mechanically difficult to support multiple coils within the reactor vessel. Reactors with internal cooling coils are thus typically used in medium size applications of between 100 and 20,000 gallons. This reactor configuration is quite common in hydrogenation systems, such as in edible oil production, and in inorganic oxidations such as copper oxidation to copper sulfate.

One approach for precluding the geometric and flow constraints on the A/V ratio is to use a sidestream cooling system for external cooling. This kind of reactor configuration is often used in the oxidation of cumene to cumene hydroperoxide for the production of phenol, and in some hydrogenation systems.

In such sidestream systems, a sidestream from the reactor is pumped through a heat exchanger or other cooling system, and the cooled reaction liquor is returned to the reactor vessel. In principle, the ratio of A/V is not limited by constraints associated with reactor geometry. However, there are other potential problems associated with such systems. Since the cooling is accomplished outside the reactor vessel, the cooler will normally operate at a temperature that is significantly lower than the reaction temperature. Thus, proportionally more heat exchange area and/or coolant flow is required. Also, in gas-liquid reactor systems, such as for air oxidation, oxygen oxidation or hydrogenation reactions, the reactant gas must be prevented from entering the external cooling system. Gas tends to disengage from the liquid and collect in pockets in high spots in the exchanger and associated piping. This reduces the effectiveness of the heat exchanger. Gas can also collect in circulation pumps and cause cavitation or gas flooding of the pump. In oxidation systems where the gas is air or oxygen, any gas build up in the external heat exchange system could create an explosion hazard. It is possible to keep the gas out of the external heat exchange loop. However, in many cases, this causes increased by-product formation due to reactant starvation in reaction systems where good mixing of reactants is important.

The A/V of bubble column reactors is typically quite high. In one configuration, which is used in the production of organic acids, the bubble column is configured like a vertical shell and tube heat exchanger. The reaction takes place on the tube side while cooling fluid is circulated on the shell side. The gas is sparged into some of the tubes. Liquid circulation is caused by the gas lift effect of the gas bubbles in the sparged tubes. Thus, there is upflow and gas liquid contacting in those tubes that are sparged. There is downflow without gas liquid contacting in the remainder of the tubes. This configuration has two disadvantages. The liquid velocity on the reactant side of the tubes is limited to the bubble rise velocity which is normally between 1 and 5 ft/sec. This velocity limitation limits the heat transfer coefficient U. Also, the downflow tubes are not exposed to reactant gas. This may cause a lower volumetric reaction rate and/or by-product formation as a result of gas starved conditions in the down flow tubes.

Another common bubble column configuration, which is common in the so-called Witten process for producing dimethyl terephthalate by successive oxidation and esterification of p-xylene, is to use vertical tubes with reactant fluid on the outside and cooling fluid on the inside. This is mechanically very difficult to implement, but it is advantageous if the required reaction volume is large. In such systems, feed gas is sparged into the bottom of the reactor. The gas tends to collect into a plume such that there is a column of rising gas in one section of the reactor and ungased downflow in the remainder. This leads to the same conditions described above, namely limited heat transfer coefficient on the reactant side, and gas starved conditions in the downflow regions. In addition, since the reactant side flow is not uniform, this configuration may give rise to hot spots in the vicinity of the gas plume. These hot spots can cause undesired by-product formation due to over oxidation.

Mass transfer considerations are also very important, particularly in gas liquid reaction systems. If mass transfer is reaction rate limiting, reactor productivity is determined by it. Also, reactant starvation caused by mass transfer limitations can cause by-product formation which lowers chemical selectivity. It is well known that these problems occur in air based chemical oxidation systems.

Air based bubble columns and stirred tank reactor systems have inherent mass transfer limitations. Oxygen mass transfer is proportional to the oxygen concentration or oxygen partial pressure in the oxygen containing gas bubble. The concentration of oxygen in an air bubble in a bubble column or a stirred tank reactor is only 21% at the sparger. As oxygen dissolves into the reaction liquid, where it is consumed by the reaction, and as liquid evaporates into the air bubble, the oxygen partial pressure in the air bubbles decreases, while the partial pressure of nitrogen, which is a component of air, and the partial pressure of evaporated organic material increases. Thus, the mass transfer driving force associated with air is inherently lower than if pure oxygen is used as the reactant gas.

In conventional stirred tank and bubble column reactor designs, the oxygen partial pressure of the exiting waste air stream must be maintained below safety limits of 5% on an organic free basis in order to prevent formation of flammable gas mixtures in the reactor vapor space. Thus gas phase oxygen concentration in conventional reactor designs is constrained between 21% at the air feed point and 5% at the waste gas exit. In bubble columns, the air is injected at the bottom of the reactor. The gas bubbles rise through the liquid, and the gas phase oxygen concentration varies from 21% at the bottom to 5% at the top of the reactor. In a well mixed stirred tank reactor, the average oxygen concentration in the system is 5% throughout. Thus, for a given operating pressure, safety concerns in conventional reactor systems severely constrain the available mass transfer driving force. The situation can be improved somewhat by raising the overall system pressure which raises the oxygen partial pressure, or by purging the headspace with relatively large amounts of an inert gas such as nitrogen, but these alternatives are generally very expensive.

The net result of the limited mass transfer driving force inherent in conventional air based reactor systems is that oxygen starved conditions, and the accompanying product selectivity penalty, are more likely to occur as reaction temperature and reactor productivity are increased.

Another factor which limits oxygen mass transfer capacity is the degree to which the oxygen containing gas bubbles are uniformly distributed within the liquid phase. If some regions of the liquid phase are not exposed to oxygen containing gas bubbles, those regions will be oxygen starved and by-product formation will occur. Hence it is crucial to have good gas bubble distribution throughout the reactor.

In conventional bubble column reactors or gas lift bubble column reactors, the gas bubbles are introduced at the bottom of the reactor. They rise through the reaction liquid due to their buoyancy. The bubbles cause a recirculating liquid flow pattern. In bubble column reactors, the flow tends to be up through the center of the reactor and down near the walls of the reactor. The oxygen containing gas bubbles tend to concentrate in the center upflow region, which leaves the outer downflow region gas starved and subject to by-product formation reactions. In gas lift bubble columns the oxygen is typically sparged into gas lifted heat transfer tubes such that there is liquid upflow in the tubes. Additional tubes without spargers are provided for recirculating flow. Oxygen starved conditions and hence by-product formation reactions prevail in the downflow tubes.

One specific example of an oxidation system where heat transfer and mass transfer are critical is the production of aliphatic acids. Aliphatic acids are produced by liquid phase reaction of an aldehyde with oxygen according to the reaction:

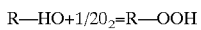

$$R\text{—}HO + 1/2 O_2 = R\text{—}OOH$$

The aldehydes and corresponding acids, may be linear or branched, and the number of carbon atoms may vary from 3 to 12. The precursor aldehydes are often made using the Low Pressure Oxo (LPO) process. Hence, the derivative acids are often referred to as Oxo acids. The aldehydes may also be obtained or produced by means other than the LPO process, but this class of compounds is referred to as Oxo acids, none the less. The source of the aldehydes is not critical to this process.

In commercial production of such acids, selectivity to acid is typically between 80% and 99%. Selectivity decreases with chain length and the number of side chains or branches. For example, the selectivity of propionaldehyde which has three carbon atoms ($C_3$), to propionic acid, is better than the selectivity of valeraldehyde to valeric acid, which has 5 carbon atoms ($C_5$); and the selectivity of valeraldehyde, which is a linear five carbon molecule, to valeric acid is higher than the selectivity of 2-methyl butyraldehyde, which is a branched $C_5$, to 2-methyl butyric acid. In commercial practice, by-product inhibitor additives may be added to some of these systems to improve selectivity.

In liquid phase aldehyde oxidation, the oxygen is typically introduced into the liquid by mass transfer from gaseous air bubbles. The oxidation reactions occur in the liquid phase; either in the bulk liquid phase or in the liquid film which surrounds the air bubbles. Oxygen starvation, that is lack of dissolved oxygen in the reaction liquid, promotes by-product formation reactions and hence reduces the selectivity of aldehyde to acid. Thus, adequate mass transfer of oxygen from the gas phase to the liquid phase is critical to maintain adequate dissolved oxygen concentration in the liquid phase in order to suppress by-product formation reactions.

It has been found that by-product formation increases with reaction temperature. Since reaction rate typically increases with temperature, the reaction consumes oxygen faster at higher temperature, and more oxygen is required to prevent the onset of oxygen starved conditions. Thus, gas-liquid mass transfer limitations become worse as temperature is increased, and therefore, it is more difficult to prevent oxygen starved conditions which cause by-product formation. The by-products formed under oxygen starved conditions are formate esters, ketones and alcohols.

Since the conversion of aldehyde to acid increases with temperature, it is possible to increase reactor productivity by increasing temperature. However, if the increase in temperature moves the reaction system into the oxygen starved regime, or makes an already oxygen starved condition worse, by-product formation reactions increase and selectivity to acid decreases.

Oxo acids are typically produced in air sparged stirred tank or bubble column gas lift reactors. At commercial reaction conditions, the exothermic heat of reaction produced by the oxidation reactions is significant. Although stirred tank reactors have been used for Oxo acid production, bubble column reactors configured as vertical shell and tube heat exchangers are preferred because of the higher A/V ratio.

In the bubble column reactors, air is sparged into the bottom of some of the heat transfer tubes, while the remainder of the tubes are not sparged. This combination of sparged and unsparged tubes causes a recirculating liquid flow within the reactor. The gas causes upflow of liquid in the sparged tubes, while downflow occurs in the remainder of the tubes that are not sparged. As air rises through the sparged tubes, oxygen transfers from the air into the liquid phase where it reacts with the aldehyde to form the acid. There is no mass transfer of oxygen into the liquid in the tubes which are not sparged.

In this reactor configuration, heat transfer occurs in all of the tubes and the ratio of A/V is high. However, the heat transfer coefficient U is limited somewhat because the tube side flow velocity is limited to the rise velocity of the gas bubbles which is typically between 1 and 5 ft/sec. Furthermore, since a fraction of the tubes are not sparged with gas these tubes operate in the mass transfer limited or oxygen starved mode. Thus, by-product formation is higher in the tubes which are not sparged compared to the tubes that are sparged. By-product formation is also favored by inherent mass transfer limitations associated with using air for the oxidant in the sparged tubes.

It will be appreciated from the above that improvements in the reactor system for oxidation, hydrogenation and other exothermic gas-liquid operations are highly desired in the art. Such improvements desirably would mitigate heat transfer limitations and improve mass transfer performance as compared to the conventional systems described above.

It is an object of the invention to provide an improved reaction system for oxidation, hydrogenation and other exothermic gas-liquid operations.

It is another object of the invention to provide a reactor system capable of mitigating heat transfer limitations and improving the mass transfer performance of exothermic gas-liquid operations.

With these and other objects in mind, the invention is hereinafter described in detail, the novel features thereof being particularly pointed out in the appended claims.

SUMMARY OF THE INVENTION

Forced circulation is utilized in conjunction with a shell and tube heat exchanger reactor to improve heat and mass transfer in exothermic reactor systems. Volumetric reactor productivity and improved selectivity are obtained thereby.

BRIEF DESCRIPTION OF THE DRAWINGS

The invention is further described in detail with respect to the accompanying drawings in which:

FIGS. 5a–5f are schematic views of another embodiment of the invention.

DETAILED DESCRIPTION OF THE INVENTION

The objects of the invention are achieved by employing a shell and tube reactor configuration such as to achieve a high heat transfer surface to reactor volume ratio A/V, together with enhanced heat transfer coefficient U, due to forced circulation of the reaction liquid. For gas-liquid reaction systems, means are provided to achieve gas circulation throughout the entire reaction volume, thereby improving reaction productivity and reaction selectivity. In its various embodiments, the invention utilizes an improved reactor system that is beneficial for conducting liquid phase reactions with two or more liquid reactants, for exothermic oxidation systems where the oxidant is either air or oxygen, for hydrogenation reactions and for other exothermic gas-liquid reaction systems. Such systems may or may not employ a solid catalyst phase.

Figure 1:
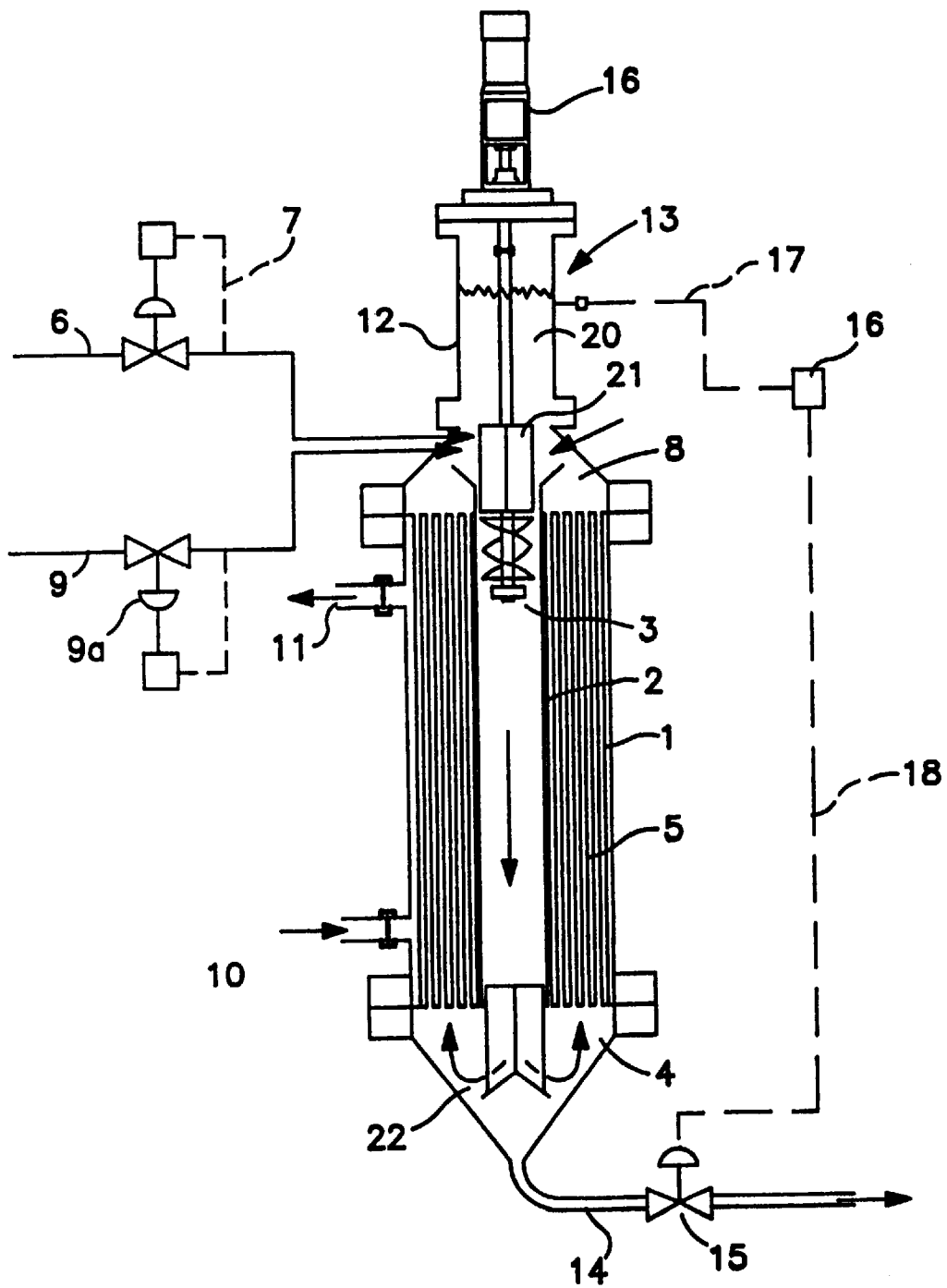
FIG. 1 is a schematic side elevational view of an embodiment of the reactor system of the invention adapted for liquid—liquid reaction.

In the embodiment of the invention illustrated on FIG. 1 of the drawings, vertical shell and tube heat exchanger reactor 1 has hollow draft tube 2 positioned in the center thereof. Impeller means 3 are positioned within said draft tube 2, and are adapted to recirculate liquid downward through the draft tube into bottom mixing chamber 4, and up through heat exchanger tubes 5. The reactor behaves much like a well mixed stirred tank reactor in that bottom mixing chamber 4 provides for bulk mixing of liquid. However, because of the pumping action of impeller means 3, the liquid is circulated through heat exchanger tubes 5 at high velocity, much like an external cooling system. Since the recirculation path is well defined and constrained by heat exchanger tubes 5, the system is not subject to flow distribution problems that can occur when a conventional stirred tank is packed with coils. The illustrated embodiment is adapted particularly for liquid—liquid reaction, with one liquid feed being passed through feed line 6 continuing that control means 7 into upper portion 8 of reactor 1, and a second liquid feed passing through feed line 9 having flow control means 9a with said upper portion 8. Cooling water is passed to reactor 1 through inlet 10, and is withdrawn through outlet 11. The liquid feed is caused to rise upward into an upper chamber 12 in fluid communication with reactor 1 so as to establish liquid level 13 thereon. Product liquid is discharged from bottom mixing chamber 4 through product discharge line 14 having control means 15. Liquid level control means 16 is in communication with upper chamber 12 to receive input signal 17 as to the liquid level in the reactor and to send output signal 18 to flow control means 15 so as to maintain the desired liquid level 13. Drive motor 19 is connected to drive shaft 20, adapted to drive impeller means 3. As illustrated, upper baffle means 21 and lower baffle means 22 are provided to facilitate the desired recirculation of liquid downward in hollow draft tube 2 and upward in said tubes 5.

The illustrated system is characterized by a high A/V ratio due to its geometric configuration, and a high heat transfer coefficient U due to the forced circulation flow. Thus, the FIG. 1 embodiment of the invention is particularly suitable for exothermic liquid phase reactions.

Figure 2:
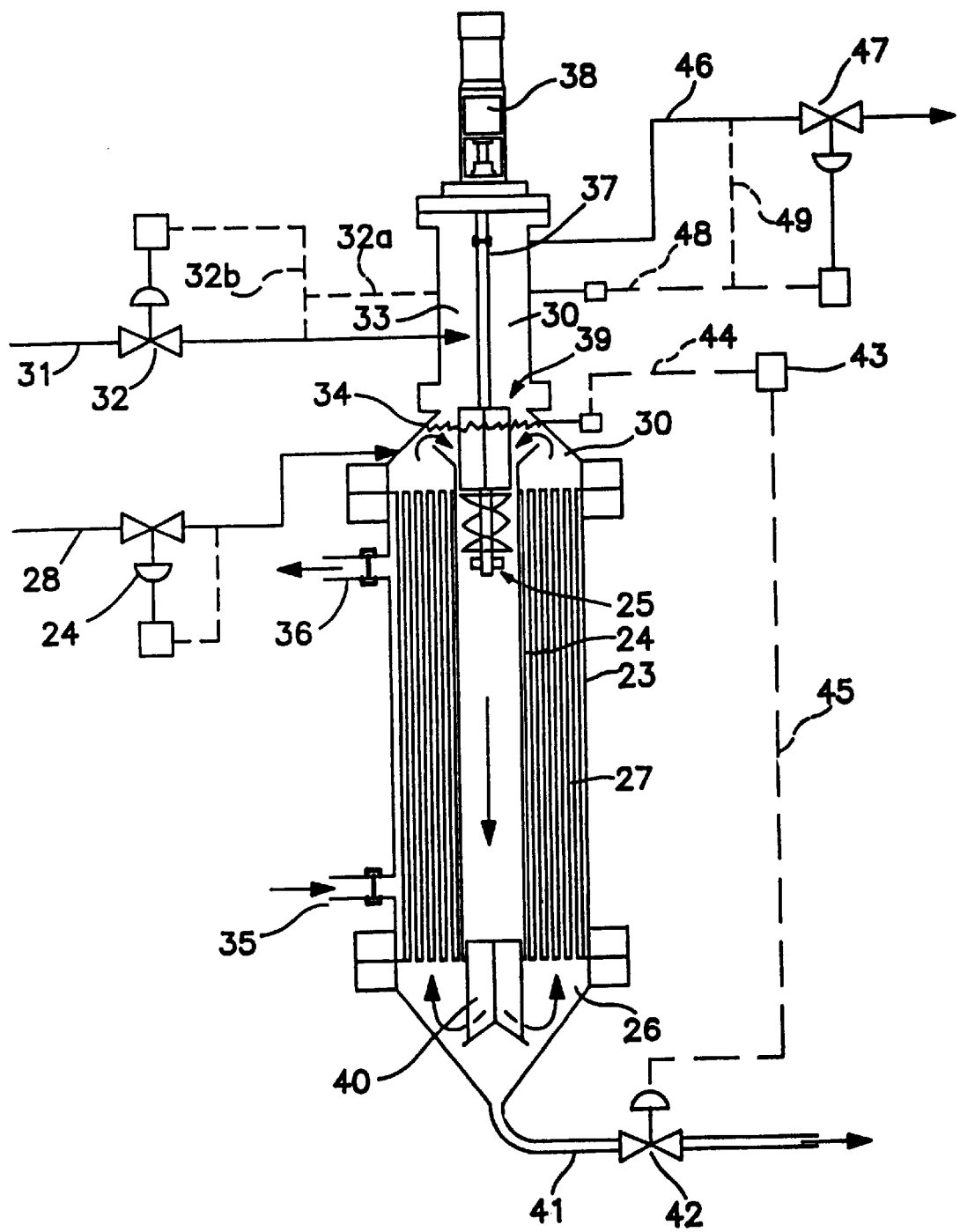
FIG. 2 is a schematic side elevational view of an embodiment of the reactor system of the invention adapted for gas-liquid reaction.

FIG. 2 illustrates an embodiment that is suitable for exothermic gas liquid reactions that are nonflammable, particularly hydrogenation reactions, and aqueous air or oxygen based oxidation reactions. In this embodiment, vertical shell and tube reactor heat exchanger reactor 23 has hollow draft tube 24 positioned in the center thereof. Impeller means 25 are positioned within draft tube 24, and is adapted to recirculate liquid downward through the draft tube into bottom mixing chamber 26 and up through heat exchanger tubes 27. Liquid feed is passed through feed line 28 containing flow control means 29 into upper portion 30 of reactor 23. Reactant gas feed is passed through line 31 containing flow control means 32 and into upper chamber 33. Said control means is adapted to control reactor pressure or feed gas flow in response to signals 32a or 32b. As will be seen from the drawing, such gas introduction is above the level of liquid, said liquid level 34 being in reactor 23 above the positioning of impeller means 25. Cooling water is introduced to reactor 23 through inlet 35 and is discharged through outlet 36. Said impeller means 25 is connected to drive shaft 37, which is driven by drive motor 38. Upper baffle means 39 and lower baffle means 40 are positioned so as to facilitate the flow of liquid into the top of hollow draft tube 24 and upward from bottom mixing chamber 26.

Reaction product is withdrawn from the bottom of reactor 23 through product discharge line 41 containing flow control means 42. Liquid level control means 43 is adapted to receive an input signal 44 from reactor 23 and to forward output signal 45 to flow control means 42 to control the liquid in reactor 23 at the desired liquid level 34. Gas is withdrawn from upper chamber 33 through line 46 containing flow control means 47 adapted for back pressure control or vent flow control as indicated by input control signals 48 and 49.

In the FIG. 2 embodiment, the reactant gas is drawn into draft tube 24 through vortex action at the upper draft tube entrance under the down pumping action of impeller means 25. Thus, the impeller means creates a gas dispersion within the liquid phase that is recirculated downward through the draft tube into bottom mixing chamber 26 and upward through heat transfer tubes 27. Unreacted reactant gas, inert nitrogen or by product gases escape into gas space 50 in upper chamber 33 above liquid level 34 wherein they become mixed with fresh feed gas and are drawn back into the recirculating body of liquid in reactor 23.

The reactor system of the FIG. 2 embodiment has a two fold advantage over conventional reactor systems. First, it has the beneficial fluid flow and heat transfer characteristics that are described above. Since the reactant gas is introduced at the top of the reactor, it is also circulated through the entire reactor volume, including all of the heat transfer tubes. Thus, all of the reactor volume is utilized for mass transfer, the reaction rate is maximized throughout the reactor, and by-product formation due to reactant gas starvation is minimized. In the case of air based reactions, mass transfer can be further enhanced by the use of oxygen feed in place of feed air.

Figure 3:
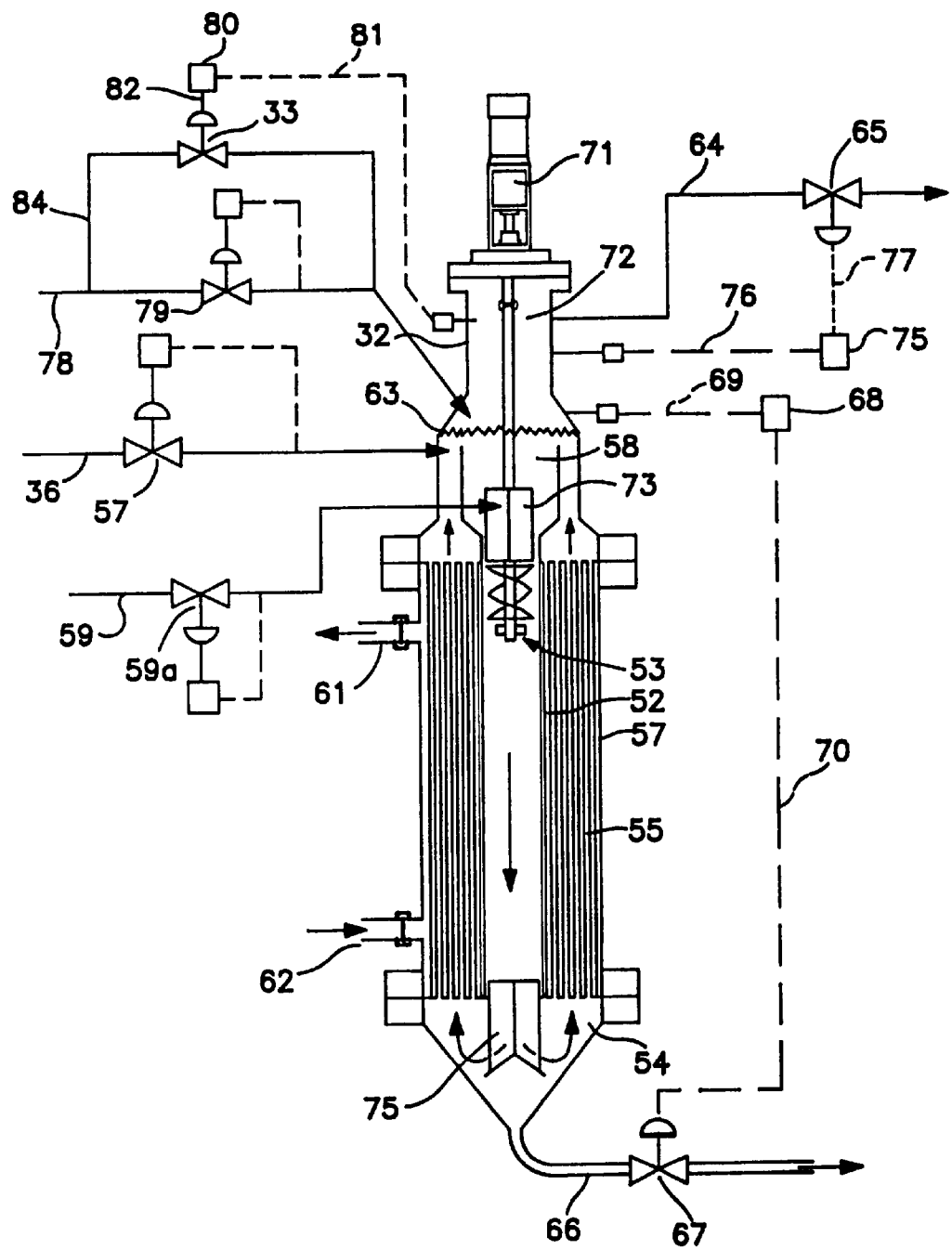
FIG. 3 is a schematic side elevational view of an embodiment of the reactor system of the invention adapted for once-through gas-liquid reaction with purge.

The embodiment of the invention illustrated in FIG. 3 of the drawings is particularly beneficial in reaction systems wherein the reactant gas can form a flammable gas mixture with the vapor above the reactant liquid, as in the air or oxygen based oxidation of organic chemicals. In such cases, the air or other reactant gas is sparged under the liquid surface directly into the impeller suction. A flammable gas mixture is formed at the point of gas injection. However, since the gas is dispersed within the liquid, it is not hazardous since flame cannot propagate through the liquid. The flow path is similar to the FIGS. 1 and 2 embodiments in that the gas liquid dispersion is pumped down through the draft tube into the bottom mixing chamber and up through the heat exchanger tubes. The gas then disengages from the liquid phase and collects in the gas space above the liquid. This configuration also takes advantage of beneficial heat transfer and fluid flow characteristics offered by the pumped shell and tube design since the reactant gas is circulated throughout the entire reactor volume. The productivity of the entire reactor volume is maximized, and the potential for reactant starved conditions that can occur in ungased tubes is minimized.

In the FIG. 3 embodiment, vertical shell and tube heat exchange reactor 51 has hollow draft tube 52 positioned in the center thereof. Impeller means 53 are positioned within said draft tube 52, preferably at the upper portion as in the other illustrated embodiments of the invention, and are adapted to recirculate liquid downward through said draft tube 52 into bottom mixing chamber 54, and up through heat exchanger tubes 55. Liquid feed is passed through feed line 56 containing flow control means 57 preferably into upper portion 58 of reactor 51. Air or an oxygen enriched feed gas is passed through feed line 59 having flow control means 59a into upper portion 58 of reactor 51, so as to be drawn into the suction of impeller means 53 along with a recirculating flow of the liquid in reactor 51. Cooling water is passed to reactor 51 through inlet 60 and is withdrawn through outlet 61. The liquid is caused to rise to a liquid level 63 in said upper portion 58, which is in fluid communication with an upper chamber 62 comprising an overhead gas phase from which gas is vented through gas discharge line 64 containing flow control means 65. Product is discharged from bottom mixing chamber 54 through line 66 containing flow control means 67. Liquid level control means 68 is adapted to receive input signals 69 as to liquid level 63 and to send output signal 70 to flow control means 67 so as to maintain the desired liquid level 63. Drive motor 71 is connected to drive shaft 72, adapted to drive impeller means 53. Upper baffle means 73 and lower baffle means 74 are provided to facilitate the desired recirculation of liquid downward in draft tube 52 and upward in said tubes 55.

In the FIG. 3 embodiment, back pressure control means 75 are provided to receive an input signal 76 as to the pressure in upper chamber 62 and to send an output signal 77 to flow control means 65 in gas discharge line 64. In addition, inert purge line 78 containing normal flow control means, e g. valve, 79 is used to introduce purge gas to upper chamber 62 or reactor 51 above liquid level 63. Oxygen analyzer 80 is adapted to receive input signals as to the oxygen concentration in upper chamber 62 and to send output signals 82 to emergency flow control means 83 to enable additional quantities of inert purge gas to flow through emergency flow line 84 to reactor 51 or upper chamber 62 above liquid level 63.

In flammable systems, the potential to form flammable gas mixtures in the waste gas stream must be eliminated. For example, in the oxidation of an organic liquid with air, the oxygen content in the waste gas must be reduced below the flammable oxygen concentration which is typically between 8% and 12%. In practice, the oxygen concentration is reduced to below 5% to provide an adequate safety margin. When air is used in this embodiment, the oxygen concentration in the gas can be reduced by reaction from 21% at the point of injection to less than 5% in the waste gas. Conventional reactors are operated in this way. Alternatively, nitrogen or other diluent gas can be added to the waste gas to reduce the oxygen concentration to less than 5%. If pure or nearly pure oxygen is used in this embodiment, the oxygen must also be reacted away or an inert diluent is added to the waste gas, as shown above, but the mass transfer performance of the system is improved due to the higher oxygen concentration.

Figure 4:
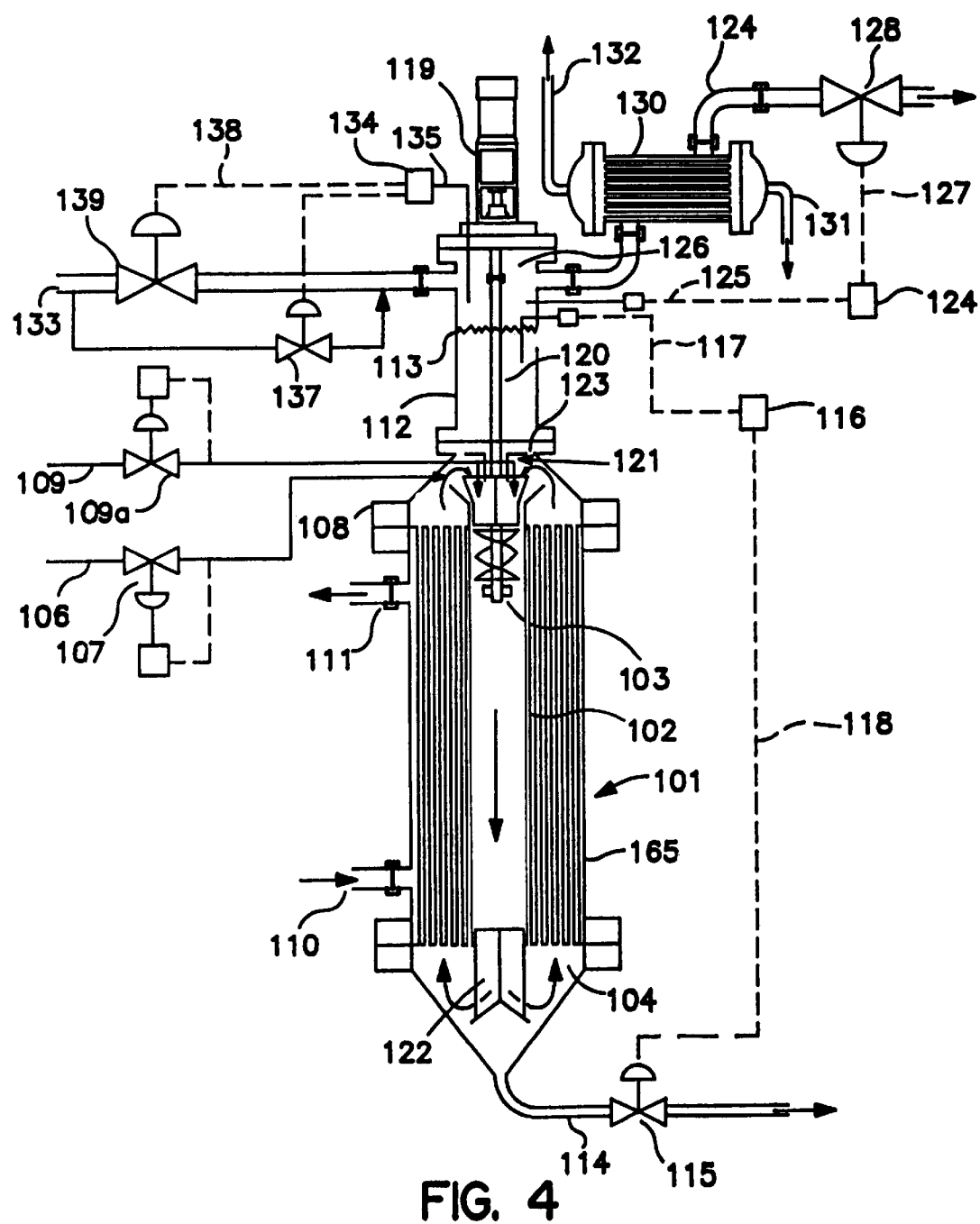
FIG. 4 is a schematic side elevational view of an embodiment of the reactor system of the invention adapted for use of impeller means for enhanced gas-liquid reaction.

FIG. 4 of the drawings shows the preferred embodiment for use in systems where the reactant gas can form a flammable gas mixture with the vapor above the liquid phase. This embodiment is particularly beneficial in the oxidation of organic chemicals with pure oxygen. In this embodiment, the oxygen is injected below the liquid surface and the flow pattern is the same as that described in the embodiment above. However, in this embodiment, a gas containment baffle is used to direct the gas flow from the top of the heat exchanger tubes back into the draft tube suction zone. Nitrogen or other inert gas is passed through the gas space above the reactor to insure that any oxygen that escapes from under the gas containment baffle is diluted to a concentration below 5%. This arrangement is a novel and advantageous modification of a conventional LOR reactor system having enhanced heat transfer capability to make the LOR system suitable for highly exothermic reactions.

In the FIG. 4 embodiment, vertical shell and tube heat exchanger reactor 101 has hollow draft tube 102 positioned in the center thereof. Impeller means 103 are positioned within said draft tube 102, and are adapted to recirculate liquid reactant downward through the draft tube into bottom mixing chamber 104, and upward through heat exchanger tubes 105. An organic liquid feed is passed through feed line 106 containing flow control means 107 into upper portion 108 of reactor 101. An oxygen feed line 109 having flow control means 109a is used to pass oxygen or an oxygen-containing gas into said upper portion 108. Cooling water is passed to reactor 101 through inlet 110, and is withdrawn through outlet 111. The organic liquid feed is caused to rise upward into upper chamber 112 so as to establish liquid level 113 therein. Product liquid is discharged from bottom mixing chamber 104 through product discharge line 114 having control means 115 therein. Liquid level control means is in communication with measuring means at upper chamber 112 to receive input signal 117 as to the liquid level in the reactor, and to send output signal 118 to flow control means 115 so as to maintain the desired liquid level 113. Drive motor 119 is connected to drive shaft 120, adapted to drive impeller means 103. Upper baffle means 121 and lower baffle means 122 are provided to facilitate the desired recirculation of liquid downward in hollow draft tube 102 and upward in said tubes 105. It should be noted that gas containment baffle 123 is positioned in the upper portion of reactor 101 above upper baffle 121. While maintaining fluid communication between the liquid in reactor 101 and the liquid in upper chamber 112, said gas containment baffle 123 serves to minimize undesired flow of unreacted gas into said upper chamber 112 to liquid level 113 and the overhead gas phase.

In the FIG. 4 embodiment, back pressure control means are provided to receive an input signal 125 as to the pressure in the gas phase 126 in upper chamber 112 and to send output signal 127 to flow control means 128 in gas discharge line 129, which contains condenser 130 to which cooling water is added through line 131 and from which cooling water is withdrawn through line 132. In addition, nitrogen or other inert gas purge line 133 is used to introduce purge gas to gas phase 126 in upper chamber 112. Oxygen analyzer 134 is adapted to receive input signals as to the oxygen concentration in said gas phase 126 and to send output signals 136 to normal purge flow control means 137 and to send output signals 138 to emergency flow control means 139 to enable additional quantities of purge gas to flow to said gas phase 136 in upper chamber 112, if needed.

In the production of Oxo acids, i.e. aliphatic acids produced by the oxidation of the corresponding aldehydes, much higher liquid circulation velocities, and therefore much higher heat transfer coefficients, are achieved using the reactor system of the invention relative to gas lift shell and tube bubble column reactors.

Oxygen was used in the reactor system of the invention to improve selectivity in the oxidation of Oxo aldehydes to the corresponding acids. With oxygen, the partial pressure of oxygen in the oxygen containing gas bubbles within the oxidation reactor is significantly greater than the inherently limited oxygen partial pressure in air. Consequently, the driving force for mass transfer is greater, and the likelihood of oxygen starved conditions which cause by-product formation is lower, with oxygen.

The subject reactor of the invention is a well mixed stirred tank reactor system, consequently oxygen bubbles are uniformly distributed throughout the liquid. Thus, with said reactor there are no zones that are oxygen starved due to poor gas liquid contacting. Also, with said reactor, the requirement that the gas bubbles have a concentration of 5% or less does not apply. Consequently, depending on the vapor pressure of the liquid which acts as a diluent, the average oxygen concentration in the gas bubbles is much higher than it is in a conventional reactor with air. In systems with a very low liquid vapor pressure, the average oxygen concentration can approach 95% or higher. This compares favorably to the average 5% oxygen concentration in a conventional air based stirred tank reactor and to the average of 13% in a bubble column reactor.

The overall higher mass transfer rate gives rise to improved oxygen mass transfer which increases the amount of oxygen available for reaction in the liquid phase and thereby reduces selectivity losses that are associated with oxygen starved conditions. The overall higher mass transfer rate also allows for operation at lower temperature and pressure than in conventional air based reaction systems. In particular, the operation at lower temperature further reduces by-product formation and increases selectivity.

A preferred practice of the invention is to use a shell and tube heat exchanger with a draft tube in the center as shown in FIG. 4. The heat load on the system is determined from the heat of reaction, the desired volumetric reaction rate and the reactor volume as shown in Equation 1. Fixing the reaction rate generally fixes the reaction temperature and pressure as well. Once the heat load, the reaction temperature and pressure are known, standard methods are used to determine U the overall heat transfer coefficient, A the required heat transfer area, and ΔT the temperature difference. These procedures are described below.

Once the reactor volume is determined, a mixing impeller/pump is chosen based on power input criteria which is required for adequate reactant mixing, and flow criteria for liquid and gas circulation. These criteria are well known to those who routinely design mixing and heat exchange equipment. For gas liquid mixing systems, the power required is usually about 5 HP/1000 gallons of liquid, but this number can vary considerably depending on the reaction system. The flow criteria are two fold. First, it is desirable to maximize flow velocity through the heat transfer tubes in order to maximize the heat transfer coefficient U. However, pressure drop through the tubes increases as the velocity squared. Thus, there is an optimum velocity for a given system. The second pumping criteria, which is important in gas liquid systems, is that the liquid velocity within the draft tube must be maintained above a minimum of 1 ft/s, but preferably above 2.5 ft/s in order to insure that the gas is drawn downward through the draft tube.

Since the reactor design is based upon the required mixing impeller/pump characteristics, the size and speed of the impeller are chosen on the basis of the required mixing power and reactor volume. This fixes the pumping characteristics for the impeller including the flow versus head curve. The heat transfer area A is estimated from Equation 2 using an estimated U. Once A and the flow are estimated, the geometry of the system can readily be determined.

The design objective is to maximize the ratio of A/V and thereby maximize the volumetric heat transfer capacity, which is turn maximizes reactor productivity. Thus small diameter heat exchanger tubes are desired. However, as tube size decreases, pressure drop within the tubes increases. Thus there is an optimum for every design case. Using the estimated flow, the heat exchanger tube diameter, number of tubes and tube length are varied to give the required A and acceptable values for pressure drop. Usually 1" or ¾" diameter heat transfer tubes are optimum.

Once the tube diameter, length and flow are known, detailed calculations for U and ΔT can be completed. The size and speed of the mixing impeller may have to be increased if the calculated U is not large enough to satisfy Equation 1. Alternatively, the heat transfer area A can be increased. Those skilled in the art of heat transfer will know how to adjust the design parameters to satisfy the heat transfer requirements. It should be noted that in the final design both heat transfer and mixing power criteria must be satisfied.

Once the impeller size is determined, and the diameter, length and number of tubes is fixed, the remainder of the reactor geometry can be completed. The draft tube diameter is fixed by the diameter of the mixing impeller. The heat transfer tubes are arranged in a standard triangular pitch around the draft tube. A triangular pitch is preferred because it gives a higher A/V than either a square pitch or a radial layout. Once the tubes are arranged the overall diameter of the reactor vessel is fixed.

The upper head geometry depends on which reactor configuration is used. In the liquid reactor configuration, and the configuration for gas liquid reactions (known as the AGR configuration), where gas is drawn down from the gas space, the main design constraint is to insure that the flow pattern across the top of the heat exchanger tubes is symmetric so as to provide an even flow distribution in the tubes. This is accomplished by using a conical outer shell in conjunction with a flared conical draft tube inlet section. This symmetric conical arrangement insures that the flow exiting the tubes accelerates gradually and uniformly such that the impeller suction draws from all of the tubes at an equal rate.

In the cases where the reactant gas is injected below the liquid surface, passes once through the reactor and the unreacted gas is vented as waste gas, the waste gas must be prevented from being entrained in the draft tube suction flow. The symmetric conical arrangement described above is also necessary. In this case, the exit of the symmetric cone arrangement must be positioned such that the flow path from the top of the cone to the draft tube suction is long enough for the bubbles to disengage from the liquid before the liquid enters the draft tube.

In cases where a gas containment baffle is used in the upper head, the symmetric conical arrangement is also required. Other design constraints related to the gas containment baffle are disclosed in the Kingsley Patent, U.S. Pat. No. 5,451,349.

The bottom mixing chamber is made from a conical or dished head of the same diameter as the heat exchanger tubesheet. A conical head is shown in the drawings. The volume of this head can be adjusted so the total reactor volume matches the desired reactor volume.

A cross baffle is used in the lower head to help insure even flow distribution across the heat exchanger tubes. The cross baffle serves to segment the discharge flow from the bottom of the draft tube into four equal parts which are directed in the radial direction.

In gas liquid reactor systems, where product is withdrawn continuously, an additional baffle is used to separate gas bubbles from the liquid product. This is not a critical part of this invention since there are many ways to accomplish this.

If the reactor system is used in a gas liquid reaction where the unreacted gas is directed into a gas space above the liquid as shown in FIGS. 2–4, the mixing impeller is positioned in the top of the draft tube so as to (1) induce the vortex action to draw gas down into the liquid phase, or (2) disperse gas which is fed under the liquid surface such as when the reactant gas forms a flammable vapor mixture with the liquid. In both cases putting the pump near the top of the draft tube and introducing the gas near the top of the draft tube insure that reactant gas is circulated throughout the reactor volume. Gas could be introduced into the bottom of the reactor in these cases but the gas would follow the upflow through the heat exchanger tubes and exit into the gas space above. The draft tube would remain ungased which would defeat one of the advantages of this system, namely the uniform distribution of gas throughout the reaction volume.

In the case of liquid reactions as shown in FIG. 1, and in the case where a gas containment baffle is used as shown in FIG. 4, the mixing impeller/pump can be placed in either the top of the draft tube or the bottom. In the liquid reactor, the primary function of the impeller is to pump liquid so its position is not critical. In the case of the gas liquid reactor system with a gas containment baffle, the gas containment baffle serves to direct unreacted gas into the draft tube where the gas is drawn downward by the liquid flow. Hence in this case, putting the impeller/pump in the bottom of the reactor does not prevent gas from being distributed uniformly throughout the reactor.

The mixing impeller/pump can be any axial flow device such as a marine propeller or a fluid foil impeller such as the Lightnin A-315. The preferred embodiment for gas liquid reactor systems is the double helical impeller described by Litz et al. in U.S. Pat. No. 4,900,480.

The advantages of the system described in FIG. 4 were demonstrated in a 280 gallon heat exchanger reactor system used in the oxidation of 2-ethylhexaldehyde to 2-ethyhexanoic acid. Oxygen was sparged into the top of the draft tube where it was dispersed by the helical mixing impeller and pumped downward through the draft tube to the bottom of the reactor. The gas liquid mixture then passed upward through the heat exchanger tubes into the upper head. The conical upper head and gas containment baffle served to direct the unreacted oxygen bubbles back into the draft tube where they were redispersed and recirculated by the mixing impeller. The aldehyde was fed continuously into the upper head of the reactor. The product acid was withdrawn continuously from the lower head.

The reactor was operated in the manner of an LOR (Liquid Organic Reactor) system as in said Litz et al, U.S. Pat. No. 4,900,480 disclosure. The gas space of the reactor above the gas containment baffle was continuously inerted with nitrogen to maintain the oxygen concentration in the gas space in a safe range.

In the test, the 280 gallon demonstration reactor was run in parallel with a train of air sparged gas lift shell and tube bubble column reactors operated in series. The advantages of the new reactor system over the existing technology are shown in the Table below. The demonstration reactor was run at the same volumetric reaction rate as the average of the air based reactors. The reaction efficiency is defined as the product of the fractional conversion of aldehyde and the selectivity of converted aldehyde to acid. The temperature and pressure variations are given as a range because the conventional reactors operate at different temperatures and pressures. The highest temperature is maintained in the reactor with the highest reaction rate in order to maintain the reaction rate and maintain a high ΔT driving force for heat transfer.

TABLE

| | |
|---|---|
| Reaction Rate | Equivalent |
| Reaction Efficiency | 2.5% Higher than Air Reactors |
| Temperature | 8° C. to 43° C. Lower than Air Reactors |
| Pressure | 30 psig to 50 psig Lower than Air Reactors |
| Volume Adjusted Waste Gas Flowrate | 36% of Air Reactor Total |

At equivalent reaction rate, the reactor system of the invention gave an overall reaction efficiency which was 2.5% higher in a single reactor than was achieved in a train of three conventional reactors operated in series. Furthermore, the operating conditions were much less severe. The subject reactor operated at from 8° C. to as much as 43° C. lower in temperature, and from 30 psig to 50 psig lower in pressure than the conventional reactors. The lower temperature operation was made practical by the improved heat transfer performance of the system. The temperature driving force ΔT can be reduced as U is increased due to higher tube side flow velocities resulting from forced circulation. Also, since the reactor was configured as an oxygen based LOR the flow rate of waste gas was reduced to only 36% of the air reactors on a reactor volume equivalent basis.

FIGS. 5a–5f disclose additional improvements to an LOR, in particular the LOR disclosed herein, as follows.

FIG. 5a illustrates the vessel 205 and the containment baffle 201. Containment baffle 201 generally includes all the features illustrated in FIG. 5a except for the vessel 205, mounting ring 206 and impeller shaft 212. Thus the containment baffle includes cross baffle 208. The cross baffles 208 in straighten the downward flow of liquid into the draft tube (not shown, but corresponding to Ref. No. 2 in FIG. 1). Note that cross baffles 208 correspond to baffles 21 in FIG. 1. The separation weir 207 (also part of the containment baffle) provides a tortuous path for the liquid to allow entrained gas bubbles to disengage.

Figure 5B:
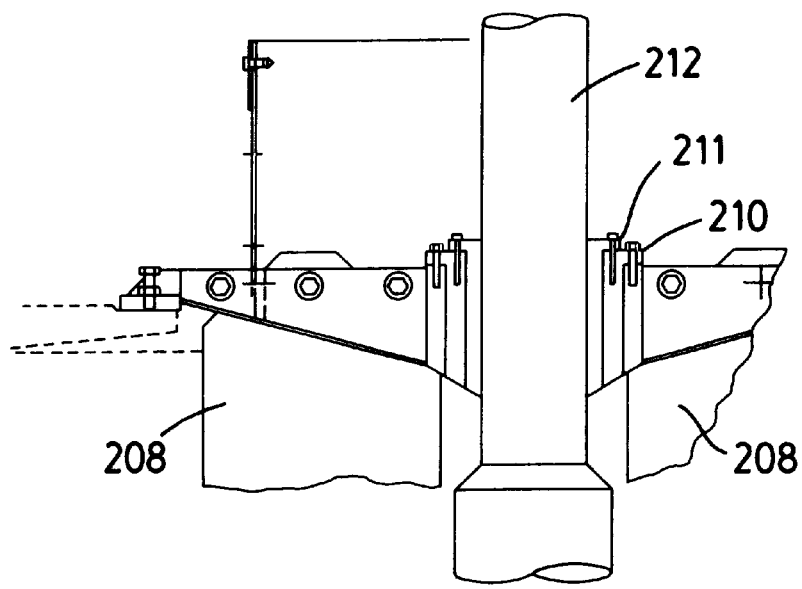
Figure 5C:
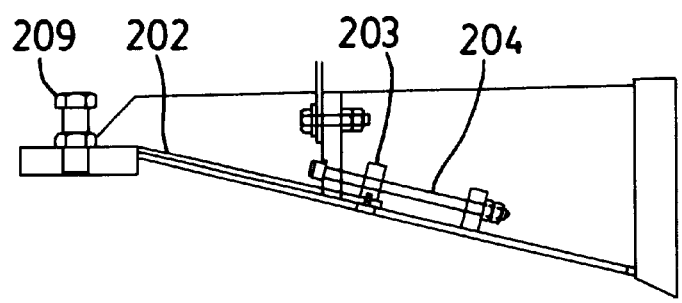
Figure 5D:
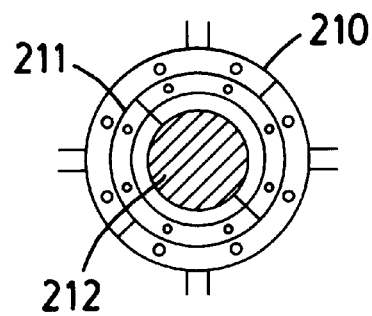

FIGS. 5b and 5d illustrates a bearing support 210 and bearing 211 to provide stability to the impeller shaft and to prevent significant cross contamination of the upper (cooler) and lower (warmer) portions of the reactor contents. (Recall that the reactor contents in the lower portion of the reactor were warmed due to exothermic reaction, and that this liquid was cooled via heat exchange during recirculation, such that the upper reactor contents are cooler than the lower). The bearing support and bearing are part of the containment baffle. The containment baffle 201 also provides the lower support of the impeller shaft 212 (See FIG. 5b). Rather than having a separate structure, the containment baffle has the strength to act as shaft support and to hold the bearing support 210 and bearing 211. The bearing material may preferably be TEFLON®.

Adjustable vent gates are particularly illustrated in FIG. 5c. In particular adjustable gate 202 is adjusted by the gate adjustment mechanism 204, and held in place by gate holder 203. These gates 202 allow the gas containment baffle 201 to be adjusted and optimized to the process. It controls the openings between the upper and lower vessel section (e.g. the quiescent zone and the active zones, respectively).

The invention also includes bearing lubrication and cooling. Heat, the amount of which is difficult to control, can build up in the steady bearing. We have found that one may provide a small amount of lubricant (e.g. an amount insignificant enough so as not to contaminate the system), preferably recirculated liquid end product from the reactor, through the impeller steady bearing in order to lubricate and cool it. This is illustrated in FIGS. 5e and 5f, which are magnified views analogous to FIG. 5b (but illustrating the cooling means).

As shown in FIG. 5e, a spiral groove 213, and cut out area 214 can be incorporated into bearing 211 in order to allow lubricant to cool the impeller shaft 212. The rotation of the shaft 212 creates suction such that the product is circulated from the top of the bearing to the bottom, via the spiral groove 213.

Figure 5F:
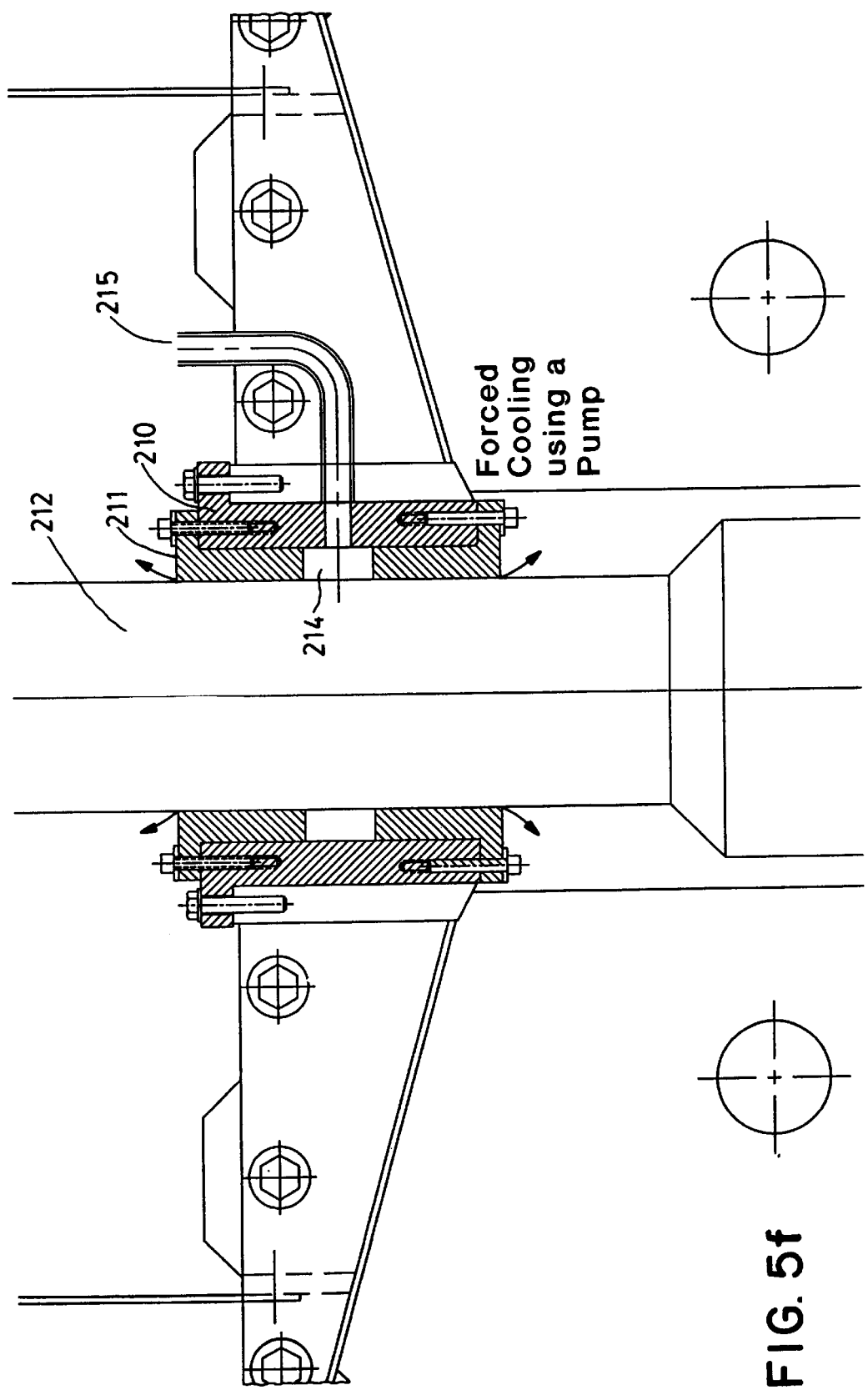

In a preferred mode, illustrated in FIG. 5f, the liquid end product forced, via the use of an external pump (not shown) via line 215, into cavity 214 of steady bearing 211 in order to cool the impeller shaft 212. The coolant flows out of the bearing 211 (between the bearing 211 and shaft 212) as indicated by the arrows. A recirculated portion of liquid end product is a preferred lubricant so as not to contaminate the reactor contents. The end product may be removed as a side-stream from the product discharge line (See FIG. 1, Ref. No. 14), cooled, circulated through external pumping means (not shown), and fed into the bearing via line 215.

It should be noted that controlling the amount of lubricant/coolant is an important consideration. The amount must be large enough so as to provide effective cooling of the bearing, but small enough so that any contamination of reactor contents is insignificant. In the case where product is used as coolant, the amount should be small enough so as to minimize any cross contamination of the upper (cooler) and lower (warmer) reactor contents such that any effect on the heat and mass transfer efficiencies obtained through the use of the disclosed/inventive reactor (as explained elsewhere in the application) are insignificant. Those skilled in the art will recognize how to determine this amount and that it is dependent upon the exothermic characteristics of the particular reaction occurring in the reactor.

From the above, it will be appreciated that the reactor system of the invention is a highly desirable advance in the art, enabling enhanced heat and mass transfer to be achieved in exothermic reactor systems. The volumetric reactor productivity can thus be maximized. Selectivity losses associated with oxygen starved conditions are also desirably reduced. The overall high mass transfer rate, which enables operation at lower temperature and pressure, advantageously reduces by-product formation and thus increases selectivity. The reactor system of the invention provides an improvement desired in the art for liquid—liquid, gas-liquid and gas-liquid-solid reaction systems that are heat and mass transfer limited, enhancing productivity and selectivity performance of operations carried out therein.

What is claimed is:

1. A process for producing aliphatic acids, said process comprising:
   A. providing a reactor including the following:
      (i) a reactor vessel which comprises providing:
         (a) a vertically positioned tube and shell reactor vessel having a hollow draft tube in the center thereof and heat exchanger tubes in the annular space between the hollow draft tube and the outer wall of the reactor vessel, said reactor vessel having an upper space above and a hollow mixing chamber below said hollow draft tube and said heat exchanger tube;
         (b) an impeller means positioned within said hollow draft tube to cause the flow of the liquid first reactant downward through the hollow draft tube into the bottom mixing chamber and upward through said heat exchanger tubes as a substantially uniform dispersion of reactants and into said upper space in the reactor vessel;
         (c) an upper chamber positioned above and in fluid communication with said reactor vessel;
         (d) a conduit means for introducing said liquid first reactant into the reactor vessel and for introducing said one of said gas and liquid second reactant into one of said reactor vessel and said upper chamber for recirculation with the liquid first reactant downward through the hollow draft tubes into the bottom mixing chamber and upward through said heat exchanger tubes into said upper space;
         (e) a conduit means for withdrawing product liquid from the reactor vessel;
         (f) a conduit means for flowing cooling fluid to the reactor vessel for the removal of exothermic heat of reaction generated within said reactor vessel;
         (g) a control means for maintaining a desired liquid level within one of said reactor vessel and said upper chamber, and
         (h) a cross baffle means located at the lower end of said hollow draft tube, and having a design such that there is even flow distribution of recirculating reactants across said heat exchanger tubes;
      (ii) a mixing impeller supported by a bearing and directed into the reactor vessel;
   B. providing a liquid aldehyde reactant in said reactor vessel;
   C. oxidizing said liquid aldehyde reactant to form an aliphatic acid;
   D. recovering a first portion of said aliphatic acid product; and
   E. recirculating a second portion of said aliphatic acid end product through said bearing in order to cool said bearing.

2. The process of claim 1 further comprises providing a baffle means at the upper end of said hollow draft tube.

3. The process of claim 1 in which providing said control means comprises maintaining a desired liquid level in said upper chamber, said conduit means for introducing one of said gas and liquid second reactant introduce a liquid second reactant into the reactor vessel.

4. The process of claim 3 which further comprises providing a baffle means at the upper end of said hollow draft tube.

5. The process of claim 1 in which said providing conduit means comprises introducing a gas second reactant into the upper chamber above said liquid level in said one of said upper chamber and upper space in the reactor vessel.

6. The process of claim 5 which further comprises providing a baffle means at the upper end of said hollow draft tube.

7. The process of claim 3 in which said providing said conduit means comprises introducing one of said gas and liquid second reactant for introducing one of air, an oxygen containing feed gas and hydrogen into the reactor vessel below said liquid level in one of said upper chamber and upper space in the reactor vessel.

8. The process of claim 7 which further comprises providing a conduit means for passing inert purge gas through said one of said upper chamber and said upper space in the reactor vessel above said liquid level.

9. The process of claim 8 which further comprises providing a baffle means at the upper end of said hollow draft tube.

10. The process of claim 9 which further comprises providing a control means to pass additional quantities of inert purge gas to said one of said upper chamber and upper space in the reactor vessel above said liquid level for emergency purposes.

11. The process of claim 1 which further comprises providing said control means for maintaining a liquid level in said upper chamber, said conduit means for introducing said one of said gas and liquid second reactant for introducing an oxygen-containing gas second reactant into said one of said upper chamber and upper space of the reactor vessel below said liquid level, and the conduit means for introducing said liquid first reactant in the reactor vessel introduce an organic liquid as said liquid first reactant.

12. The process of claim 11 which further comprises providing a gas containment baffle positioned in said one of said upper chamber, and upper space of the reactor vessel, above said impeller means, said gas containment baffle minimizing the passage of undissolved gas bubbles upward to the liquid level in the upper chamber, and to the overhead gas in said upper chamber above the liquid level.

13. The process of claim 12 which further comprises providing a baffle means at the upper and of said hollow draft tube.

14. The process of claim 11 which further comprises providing a conduit means for passing inert purge gas through said one of said upper chamber and upper space in the reactor vessel above said liquid level.

15. The process of claim 14 which further comprises providing a control means to pass additional quantities of inert purge gas to said one of said upper chamber and upper space in the reactor vessel above said liquid level for emergency purposes.

16. The process of claim 1 wherein said providing said hollow draft tube comprises providing a conically flared portion at the upper end thereof.

* * * * *